United States Patent [19]

Teraji et al.

[11] Patent Number: 4,562,179
[45] Date of Patent: Dec. 31, 1985

[54] PHOSPHOLIPID DERIVATIVES, AND PHARMACEUTICAL COMPOSITION OF THE SAME

[75] Inventors: Tsutomu Teraji, Osaka; Eishiro Todo; Norihiko Shimazaki, both of Toyonaka; Teruo Oku, Osaka; Takayuki Namiki, Minoo, all of Japan

[73] Assignee: Fujisawa Pharmaceutical Co., Ltd., Osaka, Japan

[21] Appl. No.: 482,447

[22] Filed: Apr. 6, 1983

[30] Foreign Application Priority Data

Apr. 19, 1982 [GB] United Kingdom ............... 8211284

[51] Int. Cl.$^4$ ..................... A61K 31/685; C07F 9/9
[52] U.S. Cl. ..................................... 514/77; 260/925; 260/924
[58] Field of Search ........... 260/403, 925, 945, 456 A, 260/402.5, 400, 402; 424/211, 216; 514/77

[56] References Cited

U.S. PATENT DOCUMENTS 4,221,732  9/1980  Oette et al. ..................... 260/403

FOREIGN PATENT DOCUMENTS 0035375  9/1981  European Pat. Off. .
0050460  4/1982  European Pat. Off. .
0070433  1/1983  European Pat. Off. .
0071892  2/1983  European Pat. Off. .
2619715  11/1977 Fed. Rep. of Germany ...... 260/945
2020663  11/1979 United Kingdom .

1583661  1/1981  United Kingdom ............... 260/945

Primary Examiner—Anton H. Sutto
Attorney, Agent, or Firm—Oblon, Fisher, Spivak, McClelland & Maier

[57] ABSTRACT

New phospholipid derivatives represented by the formula:

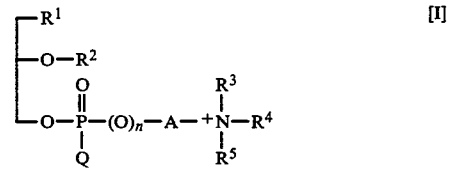

wherein
$R^1$ is alkyl, alkoxy or alkanoylamino;
$R^2$ is lower alkyl, lower alkanesulfonyl or arenesulfonyl;
$R^3$, $R^4$ and $R^5$ are each lower alkyl;
n is 0 or 1
A is lower alkylene optionally interrupted by a —NH-CO— group; and
Q is oxido or lower alkoxy;

provided that n is 0 or A is lower alkylene interrupted by a —NHCO— group, or Q is lower alkoxy, when $R^1$ is alkoxy and $R^2$ is lower alkyl; and pharmaceutically acceptable salts thereof, which exhibit antitumor activity.

8 Claims, No Drawings

PHOSPHOLIPID DERIVATIVES, AND PHARMACEUTICAL COMPOSITION OF THE SAME

This invention relates to phospholipid derivatives. More particularly, it relates to new phospholipid derivatives which have antitumor activity, to process for the preparation thereof, and to pharmaceutical composition comprising the same for therapeutical treatment of cancer.

Accordingly, one object of this invention is to provide new and useful phospholipid derivatives.

Another object of this invention is to provide process for preparation of the phospholipid derivatives.

A further object of this invention is to provide useful pharmaceutical compositions comprising said phospholipid derivatives as an antitumor agent.

Still further object of the present invention is to provide a therapeutical method of treating cancer.

With regard to the state of the art in this field for example, GB No. 1583661 reference discloses the following compound.

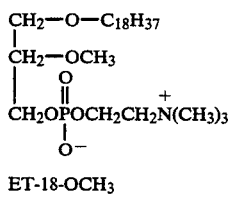

ET-18-OCH₃

It has now been found that certain phosphoryl choline derivatives which are not disclosed in any of the references have strong antitumor activity.

The object phospholipid derivatives of the present invention are novel and include the compound of the formula [I]:

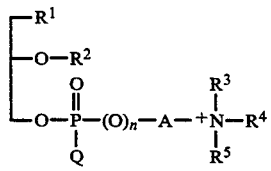

wherein
$R^1$ is alkyl, alkoxy or alkanoylamino;
$R^2$ is lower alkyl, lower alkanesulfonyl or arenesulfonyl;
$R^3$, $R^4$ and $R^5$ are each lower alkyl;
n is 0 or 1
A is lower alkylene optionally interrupted by a —NHCO— group; and
Q is oxido or lower alkoxy;
provided that n is 0 or A is lower alkylene interrupted by a —NHCO— group, or Q is lower alkoxy, when $R^1$ is alkoxy and $R^2$ is lower alkyl; and pharmaceutically acceptable salts thereof.

It is to be noted that all of the chemical formulae of the 1,2-propanediol moiety are shown by formula (A) in this specification instead of formula (B) for abbreviation sake.

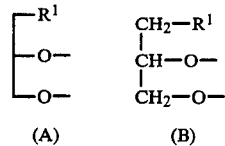

In the above and subsequent description of the present specification, suitable examples and illustrations for the various definitions to be included within the scope of the invention are explained in details as follows.

The term "lower" is intended to mean 1 to 6 carbon atom(s) and the term "higher" is intended to mean 7 to 25 carbon atoms, unless otherwise indicated.

Suitable "alkyl" is straight or branched one containing 1 to 25 carbon atoms and may include methyl, ethyl, propyl, isopropyl, butyl, isobutyl, pentyl, hexyl, heptyl, octyl, nonyl, decyl, undecyl, dodecyl, tridecyl, tetradecyl, pentadecyl, hexadecyl, heptadecyl, octadecyl, nonadecyol, eicosyl, heneicosyl, docosyl, tricosyl, tetracosyl, pentacosyl and the like, among which the preferable alkyl is the higher one having more than 10 carbon atoms, and more suitable one is higher alkyl having 15 to 18 carbon atoms.

Suitable "alkoxy" and "alkanoylamino" are illustrated as "—O-alkyl" and "—NHCO-alkyl" respectively, wherein the "alkyl" moiety is the same as exemplified above.

More suitable "alkoxy" is higher one having more than 10 carbon atoms, and the most suitable one is higher alkoxy having 15 to 18 carbon atoms.

More suitable "alkanoylamino" is higher one having more than 10 carbon atoms, and the most suitable one is higher alkanoylamino having 15 to 18 carbon atoms.

Suitable "lower alkyl" is straight or branched one such as methyl, ethyl, propyl, isopropyl, butyl, isobutyl, pentyl, hexyl or the like, among which more suitable lower alkyl is the one having 1 to 4 carbon atoms.

Suitable "lower alkanesulfonyl" is illustrated as "—SO₂-(lower)alkyl", wherein the "lower alkyl" moiety is the same as exemplified above.

Suitable "aryl" moiety in the "arenesulfonyl" may include phenyl, tolyl, xylyl, mesityl, cumenyl, naphthyl and the like. Preferable "arenesulfonyl" may be exemplified benzenesulfonyl, toluenesulfonyl, xylenesulfonyl, mesitylenesulfonyl, cumenesulfonyl, naphthalenesulfonyl or the like.

Suitable "lower alkylene" is straight or branched one containing 2 to 6 carbon atoms, and may include ethylene, trimethylene, propylene tetramethylene, pentamethylene, hexamethylene and the like, among which more suitable lower alkylene is the one containing 2 to 4 carbon atoms.

These "lower alkylene" may be interrupted by a —NHCO— group at any portion therein.

Suitable "lower alkylene interrupted by a —NHCO— group" may include
—CH₂—CH₂—NHCO—CH₂—,
—CH₂—NHCO—(CH₂)₂—,
—(CH₂)₃—NHCO—CH₂—,
—(CH₂)₂—NHCO—(CH₂)₂—,

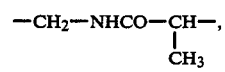

—CH₂—NHCO—(CH₂)₃—,

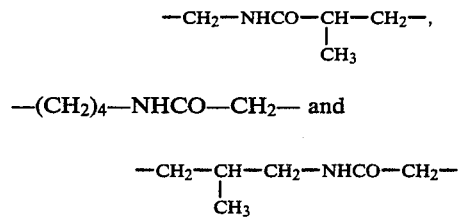

among which more suitable lower alkylene interrupted by a —NHCO— group is the one having 3 to 6 carbon atoms.

The "oxido" for Q means "O−".

Suitable "lower alkoxy" is straight or branched one such as methoxy, ethoxy, propoxy, isopropoxy, butoxy, tert-butoxy, pentyloxy, hexyloxy and the like, among which more suitable lower alkoxy is the one having 1 to 4 carbon atom(s).

It is to be noted that the compound [I], wherein Q is oxido, can alternatively be shown in an intramolecular salt form of the formula [I'].

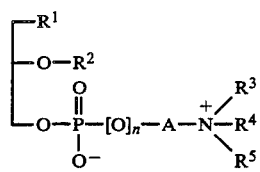

(wherein all symbols have the same meanings as defined above)

Further, the compound of formula [I], wherein Q is lower alkoxy, can alternatively be shown in a intermolecular salt form of the formula [I''].

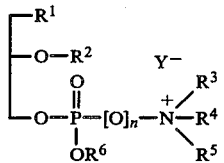

(wherein $R^1$, $R^2$, $R^3$, $R^4$, $R^5$, n and A are each as defined above, $R^6$ is lower alkyl and $Y^-$ is an anion residue of an acid)

Suitable "anion residue of an acid" for $Y^-$ may include an inorganic or organic ones such as a halide anion (e.g. chloride-, bromide-, or iodide-anion etc.), a hydroxide ion, a sulfate anion, a sulfonate anion (e.g. methanesulfonyloxy-, benzenesulfonyloxy-, tosyloxy-, or camphorsulfonyloxy-anion etc.), a carboxylate anion (e.g. trifluoroacetoxy- etc.), and the like. And further, it is also to be noted that the pharmaceutically acceptable salt of the object compound [I], wherein Q is oxido, includes an intermolecular salt as shown in the following formula [Ia] or [Ib].

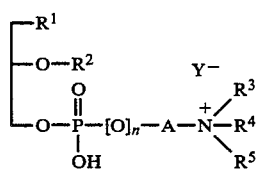

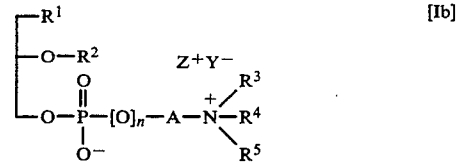

(wherein $R^1$, $R^2$, $R^3$, $R^4$, $R^5$, n, A and $Y^-$ are each as defined above, and $Z^+$ is a cation residue of a base).

Suitable "cation residue of a base" for $Z^+$ may include an alkali metal ion (e.g. sodium-, potassium-ion, etc.), alkaline earth metal ion (e.g. calcium-ion etc.) and the like.

Suitable pharmaceutically acceptable salts of the object compounds [I] are conventional non-toxic salts and may include the beforementioned salts and a salt with a base such as an alkali metal salt (e.g. sodium salt, potassium salt, etc.), alkaline earth metal salt (e.g. calcium salt etc.) and the like.

With regard to the object compounds [I], it is to be noted that the compounds [I] include all of the possible optical isomers due to the asymmetric carbon atom in the molecule of the compounds [I].

The process for preparing the object compounds [I] and salts thereof is explained in detail in the following.

The object compound [I] and its salt can be prepared by reacting a compound [II] or its salt with a compound [III] or its derivative as shown in the following scheme.

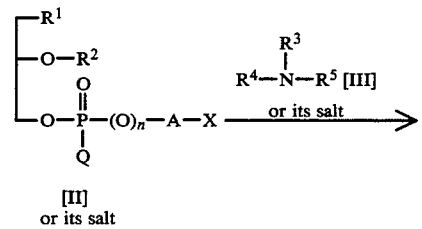

[II]
or its salt

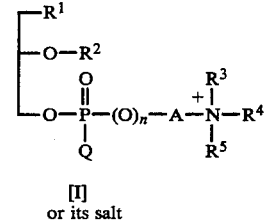

[I]
or its salt wherein
$R^1$, $R^2$, $R^3$, $R^4$, $R^5$, n, A and Q are each as defined above,
X is an acid desidue.

Suitable "acid residue" for X may be halogen (e.g. fluorine, chlorine, bromine, iodine) substituted sulfonyloxy (e.g. benzenesulfonyloxy, tosyloxy, etc.), or the like.

The suitable salt of the compound [II] is an alkali metal salt as exemplified before for the compound [I].

The suitable salt of the compound [III] are conventional non-toxic salts and may include an acid addition salt such as an inorganic acid addition salt (e.g., hydrochloride, hydrobromide, sulfate, phosphate, etc.), an organic acid addition salt (e.g., oxalate, maleate, lactate, tartrate, fumarate, methanesulfonate, benzenesulfonate, toluenesulfonate, etc.) or a solvated compound with water or an organic solvent such as tetrahydrofuran, ether, or the like.

This reaction may be carried out in a solvent such as acetone, methanol, tetrahydrofuran, chloroform, benzene or any other solvent which does not adversely affect to the reaction. In case that the compound [III] or its derivative is liquid, it can also be used as a solvent.

The reaction temperature is not critical, and the reaction is preferably carried out under warming or heating.

The object compound [I] may presumably be obtained in an acid addition salt form in the present reaction. Said compound (cf. Formula [Ia] and [Ib]) can optionally be transformed to the corresponding intramolecular salt (cf. Formula [I']) by a conventional method (e.g. treatment with an anion exchange resin, silver ion, etc.).

The object compound [I] can optionally be converted to its alkali metal salt, and further the object compound [I] can also be converted to another acid addition salt form by conventional manner.

The object compound [I] can be isolated from the reaction mixture and purified by a conventional method.

The starting compounds [II] and their salts include novel ones and can be prepared by the methods as shown in the Examples or the methods chemically equivalent thereto.

The following pharmacological data show that the object compounds [I] exhibit high anti-tumor activities.

Test Method

Groups of eight female BALB/c mice, aged 8-9 weeks and weighing 18.0-22.5 g were used.

Fibrosarcoma Meth A (hereinafter referred to as Meth A) was successively transferred every 7 days into BALB/c mice by intraperitoneal inoculation of the ascites cells thereof and the Meth A in the ascites cells as harvested 6 or 7 days after the inoculation was used as tumor cells.

Each of the BALB/c mice was inoculated intrapleurally with $5 \times 10^5$ Meth A cells in 0.1 ml Hanks solution.

Test compound was dissolved in phosphate buffer saline solution, and was injected into pleural cavity to each of the mice in doses of 100 µg/0.05 ml/mouse three times, i.e. before 14 days, after 1 hour and after 3 days of tumor implantation.

The control group was given with a vehicle alone in the same way.

The antitumor activity of the test compound was estimated by comparing mean survival time of the two groups.

T: Mean survival time of the medicated group
C: Mean survival time of the control group

| Compound Example No. | Test Results Mean survival time (Day) | Anti-tumor activity (%) *a |
|---|---|---|
| 1 - (4) | 27.5 | 458 |
| *b | 18.73 | 302.8 |

*a: T/C × 100
*b: (rac)-1-O—Octadecyl-2-O—methyl-glycerol-3-phosphorylcholine which is described in British Patent No. 1583661.

As being apparent from the above test results, the object compounds [I] of the present invention are useful as an antitumor agent.

The effective ingredient may usually be administered with a dose of 0.1 mg/kg to 500 mg/kg, 1 to 4 times a day in a preparations such as tablet, granule, powder, capsule, syrup, injection, suppository and the like. However, the above dosage may be increased or decreased according to the age, weight or conditions of the subject or the administering method.

The above mentioned pharmaceutical preparations can be prepared in a conventional manner by using conventional carriers and additives.

The present invention is illustrated by the following examples in more detail.

EXAMPLE 1

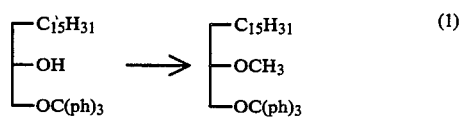

(1)

To a stirred suspension of sodium hydride (2.40 g, 60% oil dispersion, washed with dry petroleum ether) in dry tetrahydrofuran (40 ml) was portionwise added (rac)-1-O-trityl-1,2-octadecanediol (12.2 g) at ambient temperature. After the mixture was stirred for 30 minutes at the same temperature, a solution of methyl iodide (13.1 g) in dry tetrahydrofuran (40 ml) was dropwise added during a period of 45 minutes. After stirring for 3.5 hours at the same temperature, the mixture was evaporated under reduced pressure. The residue was dissolved in a mixture of diethyl ether and 0.5N aqueous sulfuric acid. The separated organic layer was dried and evaporated under reduced pressure. The residue was triturated in petroleum ether to remove impurities by filtration. The filtrate was evaporated to yield 9.8 g of (rac)-1-O-trityl-2-O-methyl-1,2-octadecanediol.

mp: 31° to 33° C.

NMR (CCl₄) ppm: 0.88 (3H, m), 1.26 (brs, 28H), 1.4 (2H, m), 3.01 (2H, m), 3.15 (1H, m), 3.30 (3H, s), 7.16-7.35 (15H, m)

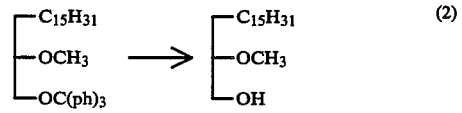

(2)

To a solution of thus obtained compound (9.5 g) in the Example-(1) in methylene chloride (100 ml) was added trifluoroacetic acid (9.5 ml) in one portion. After stirring for 8 minutes at ambient temperature, ice water (100 ml) was added thereto. The organic layer was washed with an aqueous sodium bicarbonate solution and water, dried, and evaporated under reduced pressure. The residue was treated with n-hexane (50 ml) and filtered. The filtrate was evaporated to give 4.0 of (rac)-2-O-methyl-1,2-octadecanediol.

mp: 43° to 45° C.

NMR (CDCl₃) ppm: 0.95 (3H, m), 1.25 (28H, brs), 2.05 (2H, m), 3.40 (3H, s), 3.57 (3H, m)

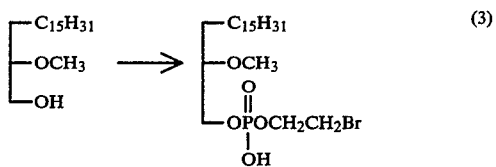

(3)

To a stirred solution of 2-bromoethyldichlorophosphate (3.46 g) in dry chloroform (10 ml) was dropwise added, during a period over 30 minutes, a solution of the compound obtained in Example 1-(2) (3.9 g) and triethylamine (3.18 g) in dry chloroform (10 ml) below 10° C. After stirring for 20 minutes at the same temperature and for an hour at ambient temperature, the mixture was cooled in an ice bath. To the resultant thick solution containing (rac)-2-O-methyl-1,2-octadecanediol-1-(2-bromoethyl)-chlorophosphate was dropwise added a mixture of water (10.5 ml) and pyridine (21 ml) below 15° C. The resulting solution was allowed to warm to ambient temperature followed by stirring for 30 minutes. The solvent was then evaporated under reduced pressure. The residue was dissolved in a mixture of an aqueous sodium bicarbonate solution and diethyl ether. The aqueous layer was washed with diethyl ether, adjusted to pH 1 with 10% hydrochloric acid, and extracted twice with ethyl acetate. The extract was washed with water, dried, and evaporated under reduced pressure to yield 4.1 g of (rac)-2-O-methyl-1,2-octadecanediol-1-(2-bromoethyl)phosphate.

mp: 62° C.

IR (film): 2900, 2840, 1235 cm$^{-1}$

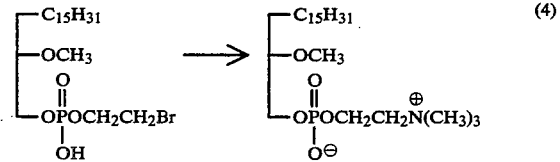

(4)

To a solution of thus obtained compound (4.0 g) in Example 1-(3) in methanol (32 ml) was added 30% aqueous trimethylamine (16.2 g) in one portion. After stirring for 1.5 hours at 50° C., the solution was allowed to stand overnight. The mixture was filtered and the filtrate was then evaporated to give (rac)-2-O-methyl-1,2-octadecanediol-1-phosphorylcholine bromide. Thus obtained compound was dissolved in 90% aqueous methanol (73 ml), and silver acetate (4.54 g) was added thereto. The solution was stirred for 1 hour at ambient temperature. The resulting precipitates were removed by filtration and washed with methanol. The combined filtrate and washings were evaporated to dryness. The residue was purified by column chromatography on silica gel (260 g, elution by chloroform-methanol-water, 65:25:4) to give 1.65 g of (rac)-2-O-methyl-1,2-octadecanediol-1-phosphorylcholine.

mp: 240° to 245° C. (dec.)

IR (Nujol): 1240 cm$^{-1}$

NMR(CDCl$_3$) ppm: 0.90 (3H, m), 1.30 (30H, brs), 3.37 (3H, s), 3.43 (9H, s), 3.82 (4H, m), 4.28 (3H, m)

Anal. Calcd. for C$_{24}$H$_{52}$O$_5$NP.2H$_2$O: C: 57.46, H: 11.25, N: 2.79. Found. C: 57.87, H: 11.34, N: 2.86.

EXAMPLE 2

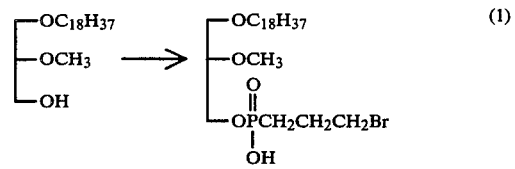

(1)

(rac)-1-O-Octadecyl-2-O-methyl-glycerol-3-(3-bromopropyl)phosphonate (3.01 g) was obtained by reacting 3-bromopropylphosphonic acid dichloride (2.64 g) with (rac)-1-O-octadecyl-2-O-methyl-glycerol (3.42 g) in a similar manner to that of Example 1-(3). Thus obtained compound was purified by column chromatography on silica gel (120 g, elution by chloroform-methanol-water, 65:25:4).

mp: 68° C.

IR (Nujol): 1090 cm$^{-1}$

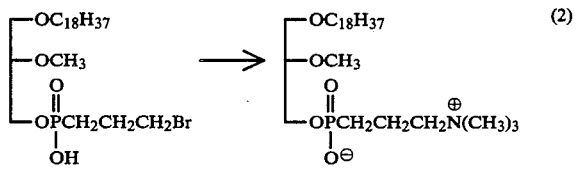

(2)

(rac)-1-O-Octadecyl-2-O-methyl-glycerol-3-(3-trimethylammoniopropyl)phosphonate (2.87 g) was obtained by reacting the compound (2.90 g) obtained in the above Example 2-(1) with 30% aqueous trimethylamine (10.5 g) in a similar manner to that of Example 1-(4).

mp: 223° to 225° C. (dec.)

IR (Nujol): 3350, 1465, 1195, 1130 cm$^{-1}$

NMR (CD$_3$OD) ppm: 0.89–1.78 (37H, m), 1.98 (2H, m), 2.96–3.62 (6H, m), 3.12 (9H, s), 3.42 (3H, s), 3.88 (1H, m)

Anal. Calcd. for C$_{28}$H$_{60}$NO$_5$P.5/2H$_2$O: C: 59.33, H: 11.20, N: 2.47. Found. C: 59.20, H: 12.09, N: 2.54.

EXAMPLE 3

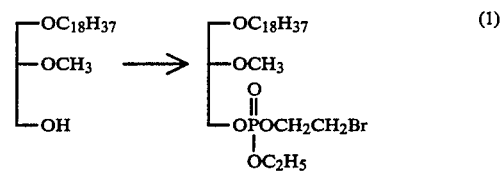

(1)

A solution of (rac)-1-O-octadecyl-2-O-methyl-glycerol (7.2 g) and triethylamine (1.82 g) in dry chloroform (10 ml) was added dropwise to a stirred solution of 2-bromoethyldichlorophosphate (4.87 g) in dry chloroform (6 ml) below 10° C. After the addition, the reaction mixture was allowed to warm to ambient temperature and stirred for 2 hours. The mixture containing (rac)-1-O-octadecyl-2-O-methyl-glycerol-3-(2-bromoethyl)chlorophosphate was again cooled to 5° C., and a mixture of ethanol (4.5 ml) and dry pyridine (9 ml) was added dropwise over 20 minutes thereto. After stirring for 30 minutes at 5° C. and for 1 hour at ambient temperature, the reaction mixture was washed with aqueous hydrochloric acid and brine, dried, and evaporated under reduced pressure. The obtained residue was purified by column chromatography on silica gel (200 g, elution by benzene, benzene/chloroform=1/1, and chloroform) to yield 10.26 g of (rac)-1-O-octadecyl-2-O-methyl-glycerol-3-(2-bromoethyl ethyl)phosphate.
mp: 30° C.
IR (film): 2900, 2850, 1270 cm$^{-1}$

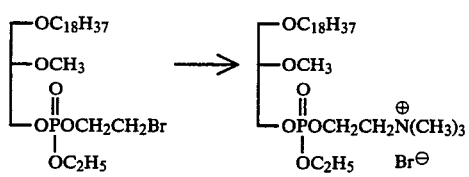

(rac)-1-O-Octadecyl-2-O-methyl-glycerol-3-(ethyl 2-trimethylammonioethyl)phosphate bromide (1.11 g) was obtained by reacting the compound (3.5 g) obtained in the above Example 3-(1) with 30% aqueous trimethylamine (12.0 g) in a similar manner to that of Example 1-(4).
mp: 218° C. (dec.)
IR (Nujol): 1260 cm$^{-1}$
NMR (CDCl$_3$) ppm: 0.89 (3H, m), 1.30 (32H, brs), 1.39 (3H, t, J=7.5 Hz), 3.47 (3H, s), 3.50 (8H, m), 3.58 (9H, s), 4.19–4.52 (5H, m)
Anal. Calcd. for C$_{29}$H$_{63}$O$_6$NBrP.H$_2$O: C: 53.53, H: 10.07, N: 2.15. Found. C: 53.18, H: 9.89, N: 1.95.

EXAMPLE 4

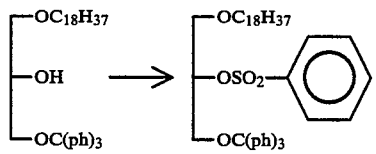

To a stirred solution of (rac)-1-O-octadecyl-3-O-trityl-glycerol (30.52 g) in a mixture of pyridine (41.08 g) and dichloromethane (250 ml) was dropwise added a solution of benzenesulfonyl chloride (18.36 g) in chloroform (50 ml) during a period of 10 minutes below 10° C. After stirring for 2 days at ambient temperature, the reaction mixture was refluxed for 8 hours. To the reaction mixture, were dropwise added pyridine (12.75 g) and benzenesulfonylchloride (5.7 g) successively. After stirring for 2 hours at room temperature, the reaction mixture was allowed to stand for 2 days. The reaction mixture was washed with water, 0.5N aqueous sulfuric acid, water, aqueous sodium bicarbonate and water, successively. The solution was dried over magnesium sulfate and evaporated under reduced pressure to give a residue, which was purified by column chromatography on silica gel (450 g, elution by benzene) to give 37.4 g of (rac)-1-O-octadecyl-2-O-benzenesulfonyl-3-O-trityl-glycerol as an oil.
NMR (CDCl$_3$) ppm: 0.85 (3H, m), 1.0–1.5 (32H, m), 3.27 (2H, t, J=6 Hz), 3.30 (2H, d, J=5 Hz), 3.59 (2H, d, J=5 Hz), 4.71 (1H, m), 7.1–7.7 (17H, m), 7.8–8.0 (3H, m)

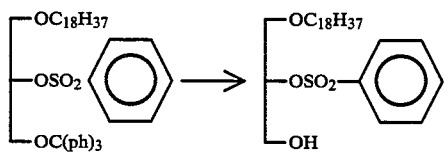

(rac)-1-O-Octadecyl-2-O-benzenesulfonyl-glycerol (19.2 g) was obtained as an oil by treating the compound (37.3 g) obtained in the above Example 4-(1) with trifluoroacetic acid (37 ml) in a similar manner to that of Example 1-(2).
NMR (CDCl$_3$): 0.88 (3H, t, J=5 Hz), 1.0–1.6 (32H, m), 2.30 (1H, m), 3.2–3.9 (6H, m), 4.70 (1H, m), 7.1–7.5 (3H, m), 7.7–8.0 (2H, m)

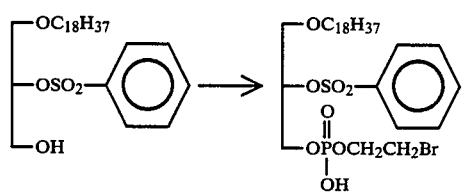

(rac)-1-O-Octadecyl-2-O-benzenesulfonyl-glycerol-3-(2-bromoethyl)phosphate (11.1 g) was obtained as an oil by reacting the compound (7.76 g) obtained in the above Example 4-(2) with 2-bromoethyldichlorophosphate (3.87 g) in a similar manner to that of Example 1-(3).
NMR (CDCl$_3$) ppm: 0.88 (3H, t, J=5 Hz), 1.1–1.6 (32H, m), 3.3–5.0 (11H, m), 7.5–7.7 (3H, m), 7.9–8.1 (2H, m), 9.02 (1H, brs)

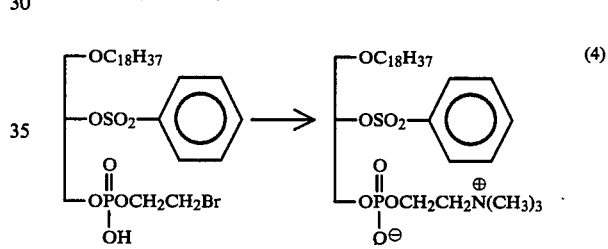

(rac)-1-O-Octadecyl-2-O-benzenesulfonyl-glycerol-3-phosphorylcholine (6.2 g) was obtained by reacting the compound (11.0 g) obtained in the above Example 4-(3) with 30% aqueous trimethylamine (32.2 g) in a similar manner to that of Example 1-(4).
Mp: 205° to 210° C.
IR (Nujol): 3360, 1240, 1180 cm$^{-1}$
NMR (CD$_3$OD) ppm: 0.90 (3H, t, J=5 Hz), 1.2–1.6 (32H, m), 3.26 (9H, s), 3.5–5.0 (11H, m), 7.4–8.1 (5H, m)
Anal. Calcd. for C$_{32}$H$_{60}$NO$_8$PS.H$_2$O: C: 57.55, H: 9.36, N: 2.10. Found. C: 57.75, H: 9.44, N: 1.99.

EXAMPLE 5

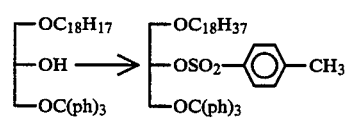

(rac)-1-O-Octadecyl-2-O-tosyl-3-O-trityl-glycerol (10.0 g) was obtained by reacting (rac)-1-O-octadecyl-3-O-trityl-glycerol (20.54 g) with tosyl chloride (13.35 g) in a similar manner to that of Example 4-(1).
Mp: 48° to 52° C.
IR (Nujol): 1655, 1170 cm$^{-1}$

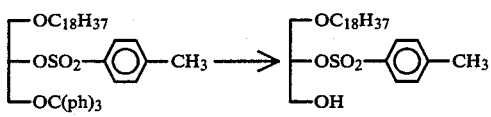

(rac)-1-O-Octadecyl-2-O-tosyl-glycerol (6.22 g) was obtained as an oil by treating the compound (9.0 g) obtained in the above Example 5-(1) with trifluoroacetic acid (9 ml) in a similar manner to that of Example 1-(2).

IR (CHCl$_3$): 3500, 2920, 2850, 1595 cm$^{-1}$

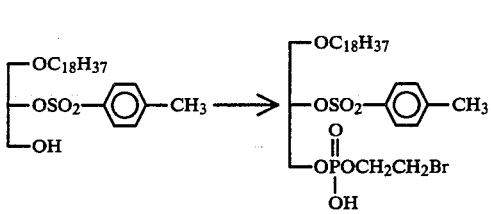

(rac)-1-O-Octadecyl-2-O-tosyl-glycerol-3-(2-bromoethyl)phosphate (6.7 g) was obtained as an oil by reacting the compound (6.07 g) obtained in the above Example 5-(2) with 2-bromoethyldichlorophosphate (2.95 g) in a similar manner to that of Example 1-(3).

IR (film): 2910, 2840, 1595, 1460, 1235 cm$^{-1}$

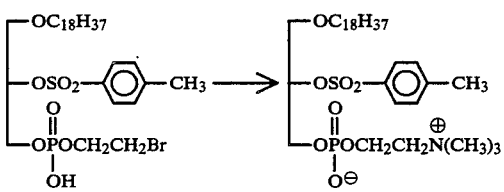

(rac)-1-O-Octadecyl-2-O-tosyl-glycerol-3-phosphorylcholine (4.0 g) was obtained by reacting the compound (6.6 g) obtained in the above Example 5-(3) with a 26% solution of trimethylamine in tetrahydrofuran (21.83 g) in a similar manner to that of Example 1-(4).

Mp: 190° C.

IR (CHCl$_3$): 3350, 1595, 1460, 1350 cm$^{-1}$

NMR (CD$_3$OD) ppm: 0.89 (3H, t, J=5 Hz), 1.06–1.52 (32H, m), 2.44 (3H, s), 3.24 (9H, s), 3.24–4.73 (11H, m), 7.40 (2H, d, J=8 Hz), 7.80 (2H, d, J=8 Hz)

Anal. Calcd. for C$_{33}$H$_{62}$NO$_8$PS.3/2H$_2$O: C: 57.30, H: 9.46, N: 2.02. Found. C: 57.20, H: 9.25, N: 2.01.

EXAMPLE 6

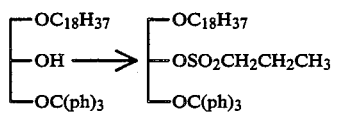

(rac)-1-O-Octadecyl-2-O-propanesulfonyl-3-O-tritylglycerol (4.6 g) was obtained as an oil by reacting (rac)-1-O-octadecyl-3-O-trityl-glycerol (30.52 g) with propanesulfonyl chloride (14.82 g) in a similar manner to that of Example 4-(1).

IR (film): 3540, 3050, 2900, 1595 cm$^{-1}$

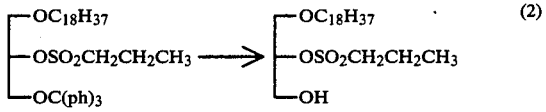

(rac)-1-O-Octadecyl-2-O-propanesulfonyl-glycerol (2.1 g) was obtained as an oil by treating the compound (4.5 g) obtained in the above Example 6-(1) with trifluoroacetic acid in a similar manner to that of Example 1-(2).

IR (CHCl$_3$): 3450, 1460, 1360 cm$^{-1}$

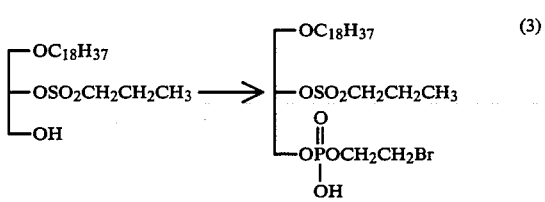

(rac)-1-O-Octadecyl-2-O-propanesulfonyl-glycerol-3-(2-bromoethyl)phosphate (2.9 g) was obtained as an oil by reacting the compound (2.1 g) obtained in the above Example 6-(2) with 2-bromoethyldichlorophosphate (1.13 g) in a similar manner to that of Example 1-(3).

IR (film): 1210 cm$^{-1}$

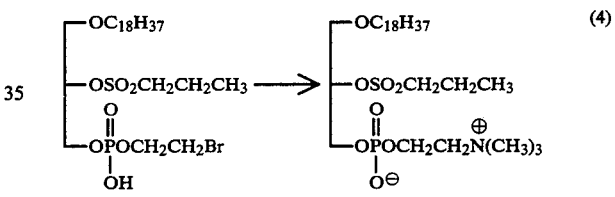

(rac)-1-O-Octadecyl-2-O-propanesulfonyl-glycerol-3-phosphorylcholine (1.9 g) was obtained by reacting the compound (2.8 g) obtained in the above Example 6-(3) with 30% aqueous trimethylamine (8.64 g) in a similar manner to that of Example 1-(4).

Mp: 203° to 206° C.

IR (Nujol): 1650, 1240 cm$^{-1}$

NMR (CD$_3$OD) ppm: 0.89 (3H, t, J=5 Hz), 1.08 (3H, t, J=7.5 Hz), 1.19–1.75 (32H, m), 1.88 (2H, m), 3.04–4.86 (13H, m), 3.23 (9H, s)

Anal. Calcd. for C$_{29}$H$_{62}$NO$_8$PS.3/2H$_2$O: C: 54.18, H: 10.19, N: 2.17. Found. C: 54.08, H: 10.44, N: 2.10.

EXAMPLE 7

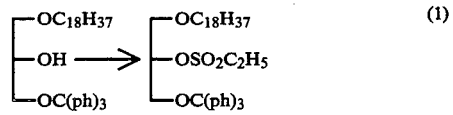

(rac)-1-O-Octadecyl-2-O-ethanesulfonyl-3-O-tritylglycerol (32.2 g) was obtained as an oil by reacting (rac)-1-O-octadecyl-3-O-trityl-glycerol (30.52 g) with ethanesulfonyl chloride (13.36 g) in a similar manner to that of Example 4-(1).

NMR (CDCl$_3$) ppm: 0.88 (3H, t, J=5 Hz), 1.0–1.8 (35H, m), 3.17 (2H, q, J=6.5 Hz), 3.2–5.0 (7H, m), 7.1–7.5 (15H, m)

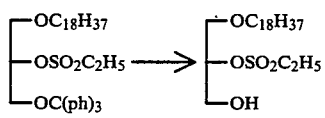 (2)

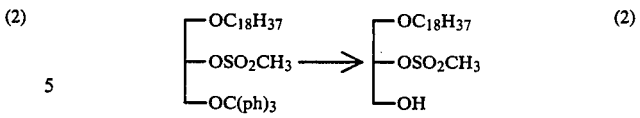 (2)

(rac)-1-O-Octadecyl-2-O-ethanesulfonyl-glycerol (14.87 g) was obtained as an oil by treating the compound (32.0 g) obtained in the above Example 7-(1) with trifluoroacetic acid (32 ml) in a similar manner to that of Example 1-(2).

NMR (CDCl$_3$) ppm: 0.89 (3H, t, J=6 Hz), 1.0–1.7 (35H, m), 2.43 (1H, t, J=6 Hz), 3.1–4.9 (9H, m)

(rac)-1-O-Octadecyl-2-O-methanesulfonyl-glycerol (10.3 g) was obtained as a waxy solid by treating the compound (35 g) obtained in the above Example 8-(1) with conc. hydrochloric acid (26.4 ml) in a similar manner to that of Example 1-(2).

IR (CHCl$_3$): 3400, 2970, 2860, 1600 cm$^{-1}$

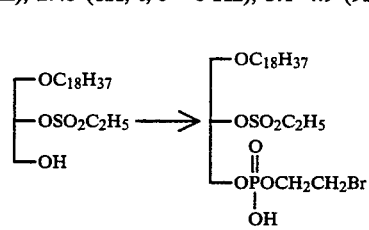 (3)

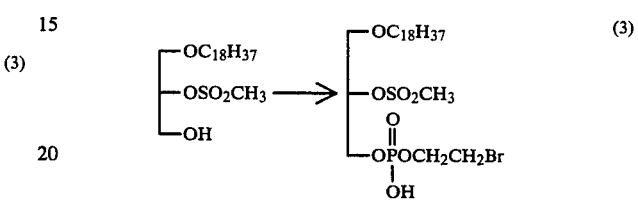 (3)

(rac)-1-O-Octadecyl-2-O-ethanesulfonyl-glycerol-3-(2-bromoethyl)phosphate (8.6 g) was obtained as an oil by reacting the compound (6.99 g) obtained in the above Example 7-(2) with 2-bromoethyldichlorophosphate (3.87 g) in a similar manner to that of Example 1-(3).

NMR (CDCl$_3$) ppm: 0.88 (3H, t, J=5 Hz), 1.0–2.0 (35H, m), 3.25–5.0 (13H, m), 10.02 (1H, brs)

(rac)-1-O-Octadecyl-2-O-methanesulfonyl-glycerol-3-(2-bromoethyl)phosphate (6.7 g) was obtained as an oil by reacting the compound (7.9 g) obtained in the above Example 8-(2) with 2-bromoethyldichlorophosphate (4.52 g) in a similar manner to that of Example 1-(3).

IR (film): 2920, 2850, 1215 cm$^{-1}$

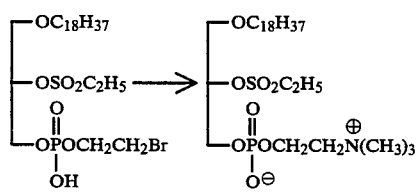 (4)

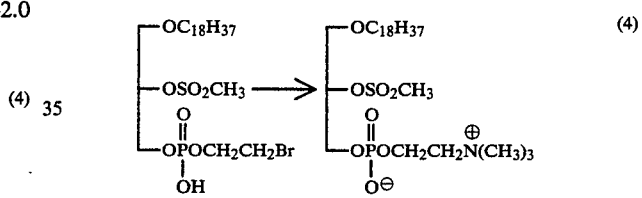 (4)

(rac)-1-O-Octadecyl-2-O-ethanesulfonyl-glycerol-3-phosphorylcholine (3.51 g) was obtained by reacting the compound (8.23 g) obtained in the above Example 7-(3) with 35% aqueous trimethylamine (22.3 g) in a similar manner to that of Example 1-(4).

Mp: 220° C.

IR (Nujol): 3350, 1650, 1225 cm$^{-1}$

NMR (CD$_3$OD) ppm: 0.90 (3H, t, J=6 Hz), 1.1–1.7 (35H, m), 3.26 (9H, s), 3.3–4.9 (13H, m)

Anal. Calcd. for C$_{28}$H$_{60}$NO$_8$PS.H$_2$O: C: 54.26, H: 10.08, N: 2.25. Found. C: 54.23, H: 10.02, N: 2.16.

EXAMPLE 8

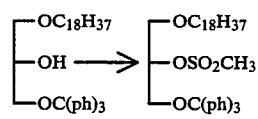 (1)

(rac)-1-O-Octadecyl-2-O-methanesulfonyl-3-O-tritylglycerol (35.9 g) was obtained as an oil by reacting (rac)-1-O-octadecyl-3-O-trityl-glycerol (30.52 g) with methanesulfonyl chloride (11.91 g) in a similar manner to that of Example 4-(1).

IR (film): 3060, 3030, 2930, 1598 cm$^{-1}$ (rac)-1-O-Octadecyl-2-O-methanesulfonyl-glycerol-3-phosphorylcholine (4.1 g) was obtained by reacting the compound (6.6 g) obtained in the above Example 8-(3) with 35% aqueous trimethylamine (19.3 g) in a similar manner to that of Example 1-(4).

Mp: 188° C.

IR (Nujol): 3400, 1650, 1340 cm$^{-1}$

EXAMPLE 9

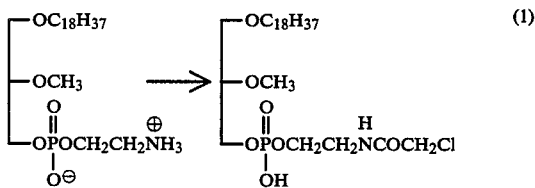 (1)

To a stirred suspension of (rac)-1-O-octadecyl-2-O-methyl-glycerol-3-(2-aminoethyl)phosphate (5.3 g) in dry chloroform (88 ml) was added bis(trimethylsilyl)acetamide (4.47 g) in one portion with stirring at ambient temperature followed by stirring for another one hour. The resulting solution was cooled in an ice bath and a solution of chloroacetyl chloride (1.37 g) in dry chloroform (22 ml) was dropwise added during a period of 5 minutes with stirring. After stirring for 3 hours at 5° C., the reaction mixture was washed with aqueous hydrochloric acid and with brine, dried, and evaporated under reduced pressure. The residue was crystallized from n-hexane to yield 5.4 g of (rac)-1-O-octadecyl-2-O-methyl-glycerol-3-[2-(2-chloroacetylamino)ethyl]phosphate.

IR (Nujol): 3300, 1640, 1220 cm$^{-1}$

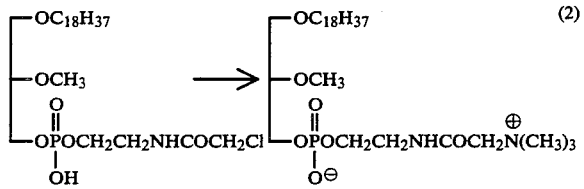

(rac)-1-O-Octadecyl-2-O-methyl-3-[2-(2-trimethylammonioacetylamino)ethyl]phosphate (1.8 g) was obtained by reacting the compound (2.0 g) obtained in the above Example 9-(1) with 26% solution of trimethylamine in tetrahydrofuran (8.12 g) in a similar manner to that of Example 1-(4).

Mp: 226° to 230° C.

IR (Nujol): 3350, 1680 cm$^{-1}$

NMR (CDCl$_3$) ppm: 0.89 (3H, m), 1.07–1.42 (32H, m), 3.21–3.59 (18H, m), 3.66–4.07 (5H, m), 4.24–4.51 (2H, m), 10.06 (1H, m)

Anal. Calcd. for C$_{29}$H$_{61}$N$_2$O$_7$P.H$_2$O: C: 57.94, H: 10.60, N: 4.46. Found. C: 58.16, H: 10.60, N: 4.48.

EXAMPLE 10

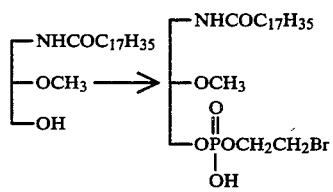

(rac)-2-O-Methyl-3-octadecanoylamino-1,2-propanediol-1-(2-bromoethyl)phosphate (5.81 g) was obtained by reacting (rac)-2-O-methyl-3-octadecanoylamino-1,2-propanediol (6.5 g) with 2-bromoethyldichlorophosphate (4.35 g) in a similar manner to that of Example 1-(3).

Mp: 89° to 94° C.

IR (Nujol): 3300, 1635, 1220 cm$^{-1}$.

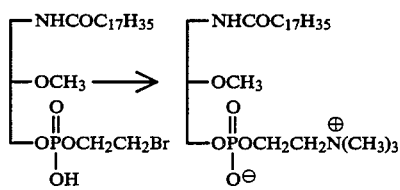

(rac)-2-O-Methyl-3-octadecanoylamino-1,2-propanediol-1-phosphorylcholine (3.21 g) was obtained by reacting the compound (5.58 g) obtained in the above Example 10-(1) with 35% aqueous trimethylamine (16.85 g) in a similar manner to that of Example 1-(4).

Mp: 100° C.

IR (Nujol): 3300, 1640, 1220 cm$^{-1}$

NMR (CD$_3$OD) ppm: 0.90 (3H, t, J=7 Hz), 1.06–1.78 (30H, m), 2.20 (2H, t, J=7 Hz), 3.10–4.40 (9H, m), 3.26 (9H, s), 3.43 (3H, s)

Anal. Calcd. for C$_{27}$H$_{57}$O$_6$N$_2$P.H$_2$O: C: 58.45, H: 10.72, N: 5.05. Found. C: 57.85, H: 10.67, N: 4.82.

What is claimed is:

1. A compound of the formula:

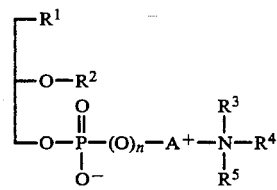

wherein

R$^1$ is higher alkyl or higher alkoxy;

R$^2$ is lower alkyl;

R$^3$, R$^4$ and R$^5$ are each lower alkyl;

n is 0 or 1; and

A is lower alkylene optionally interrupted by a —NHCO— group;

provided that n is 0, or A is lower alkylene interrupted by a —NHCO— group, when R$^1$ is higher alkoxy;

or a pharmaceutically acceptable salt thereof.

2. A method for treating fibrosarcoma Meth A which comprises administering an effective amount of the compound of claim 1 to a subject in need of said treatment.

3. The compound according to claim 1, which is (rac)-1-O-octadecyl-2-O-methyl-glycerol-3-(3-trimethylammoniopropyl)phosphonate.

4. A compound according to claim 1, wherein A is lower alkylene interrupted by a —NHCO— group.

5. The compound according to claim 4, which is (rac)-1-O-octadecyl-2-O-methyl-3-[2-(2-trimethylammonioacetylamino)ethyl]phosphate.

6. A compound according to claim 1, wherein R$^1$ is higher alkyl, R$^2$ is lower alkyl, n is 1 and A is lower alkylene.

7. The compound according to claim 6, which is (rac)-2-O-methyl-1,2-octadecanediol-1-phosphorylcholine.

8. A pharmaceutical composition for treating fibrosarcoma Meth A, comprising an effective amount of the compound of claim 1, in association with a pharmaceutically acceptable carrier or excipient.

* * * * *